United States Patent [19]

Sawai et al.

[11] Patent Number: 4,544,772
[45] Date of Patent: Oct. 1, 1985

[54] METHOD OF PURIFYING HEXAFLUOROACETONE HYDRATE

[75] Inventors: Mithio Sawai; Yoshihiro Tasaka, both of Kamifukuoka; Toshikazu Kawai; Yutaka Katsuhara, both of Kawagoe, all of Japan

[73] Assignee: Central Glass Company, Limited, Ube, Japan

[21] Appl. No.: 604,536

[22] Filed: Apr. 27, 1984

[30] Foreign Application Priority Data

Apr. 30, 1983 [JP] Japan ................................. 58-74924

[51] Int. Cl.⁴ ............................................. C07C 45/80
[52] U.S. Cl. ..................................... 568/411; 568/842
[58] Field of Search ............................... 568/842, 411

[56] References Cited

U.S. PATENT DOCUMENTS

| | | | |
|---|---|---|---|
| 3,433,838 | 3/1969 | Cunningham et al. | 568/411 |
| 3,544,633 | 1/1970 | Yodis et al. | 568/411 |
| 3,632,652 | 1/1972 | Chu et al. | 568/411 |
| 4,386,223 | 5/1983 | Kawai et al. | 568/411 |

*Primary Examiner*—James H. Reamer
*Attorney, Agent, or Firm*—Fleit, Jacobson, Cohn & Price

[57] ABSTRACT

Crude hexafluoroacetone (HFA) hydrate containing chlorofluoroacetone(s) hydrate(s) as impurity is purified by adding an alkali metal hydroxide and maintaining at an elevated temperature, preferably at 100°–110° C., to thereby cause decomposition reaction of every chlorofluoroacetone hydrate with the alkali metal hydroxide, followed by neutralization of an excess portion of the alkali metal hydroxide. Alkali metal hydroxides, which readily react with anhydrous HFA, react preferentially with chlorofluoroacetone hydrates but hardly react with coexisting HFA hydrate.

5 Claims, No Drawings

METHOD OF PURIFYING HEXAFLUOROACETONE HYDRATE

BACKGROUND OF THE INVENTION

This invention relates to a method of purifying hexafluoroacetone hydrate containing hydrates of chlorofluoroacetones as impurities.

Hexafluoroacetone (abbreviated to HFA) is known as an important intermediate for the preparation of some fluorine-containing polymers and a variety of useful organic compounds including medicines and agricultural chemicals. HFA is a toxic gaseous compound of which the boiling point is −28° C. and, therefore, must be handled very cautiously when storing and transporting.

HFA readily reacts with water to form a monohydrate, which is a solid having a melting point of 46° C., as represented by Equation (1).

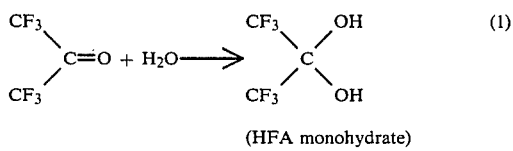

(HFA monohydrate)

The monohydrate easily dissolves in excess water to undergo further hydration. When the mole ratio of water to HFA is about 3, the hydrate (hereinafter referred to as "HFA.3H$_2$O") is a constant boiling mixture of which the boiling point is 106° C. HFA.3H$_2$O is a stable liquid easy to store and transport, and anhydrous HFA can easily be recovered from HFA.3H$_2$O by a simple dehydration reaction using a suitable dehydrating agent such as concentrated sulfuric acid or phosphorus pentoxide. Besides, HFA.3H$_2$O itself has unique properties as a solvent. Therefore, HFA hydrate is attracting increasing attention.

Usually HFA is prepared by reaction of hexachloroacetone with hydrogen fluoride gas in the presence of catalyst such as chromium trifluoride or dichromium trioxide. The gaseous product of the reaction contains unreacted hydrogen fluoride and by-produced hydrogen chloride, and these hydrogen halides tend to react with HFA to form complexes. According to U.S. Pat. No. 4,386,223, the hydrogen halides can be removed by first hydrating the crude HFA gas and then neutralizing the hydrogen halides in the hydrated material by using a calcium compound such as CaCO$_3$, Ca(OH)$_2$ or CaO as a neutralizing agent.

In the preparation of HFA from hexachloroacetone it is inevitable that the crude HFA gas contains some amounts of organic by-products, which are principally chlorofluoroacetones (hereinafter referred to as "FK's") such as chloropentafluoroacetone (hereinafter referred to as "5FK"), dichlorotetrafluoroacetone (referred to as "4FK") and trichlorotrifluoroacetone (referred to as "3FK"). Since these FK's are high in toxicity and, like HFA, also in reactivites it is desirable to completely separate the FK's from HFA. Like HFA, most of these FK's tend to form complexes with hydrogen halides and, moreover, readily react with water to form their respective hydrates. It is difficult to separate such FK's hydrates from HFA hydrate because the FK's hydrates have boiling points ranging from about 105° C. to about 106° C., which are very close to the boiling point of HFA.3H$_2$O. The aforementioned U.S. Pat. No. 4,386,223 proposes to decompose the FK's hydrates coexisting with HFA hydrate by using an alkali metal carbonate, alkaline earth metal hydroxide or alkaline earth metal oxide as a decomposing agent.

In theory it is possible to separate FK's from HFA, without hydrating them, by distillation utilizing differences in boiling points of the respective fluoroacetones, but in practice this method is disadvantageous in some respects such as the need of pressure distillation and the intricateness of the process.

A major cause of the difficulty in purifying HFA is that HFA itself exhibits high reactivities. Besides the reactions with hydrogen halides to form complexes, HFA readily undergoes a decomposition reaction with an alkali compound such as KOH or NaOH. As homologous compounds FK's also exhibit nearly similarly high reactivities, so that it has been accepted as to be very difficult to separate FK's from HFA by utilizing a certain difference in chemical reactivities. For example, separation or removal of FK's from crude HFA gas by decomposition with an alkali hydroxide such as NaOH is impractical because a decomposition reaction of HFA takes place simultaneously and proceeds competitively so that a large amount of HFA is lost during complete decomposition of the FK's.

SUMMARY OF THE INVENTION

It is an object of the present invention to provide an industrially favorable method of purifying crude HFA hydrate by removing the coexisting FK's hydrates without losing a large amount of HFA hydrate.

A method according to the invention for purifying crude HFA hydrate containing at least one FK hydrate comprises the steps of (a) adding an alkali metal hydroxide to the crude HFA hydrate and maintaining the resultant mixed solution at an elevated temperature to thereby cause preferential decomposition of every FK hydrate with the alkali metal hydroxide, (b) neutralizing an excess portion of the alkali metal hydroxide by adding a mineral acid to the reaction liquid after step (a), and (c) recovering purified HFA hydrate from the reaction liquid after step (b).

It is preferable that the mole ratio of the alkali metal hydroxide to the total of FK's hydrates in the crude HFA hydrate is in the range from 4:1 to 10:1 and that the alkali metal hydroxide amounts to 30–70 mole% of the total organic matter in the crude HFA hydrate. It is also preferable that the elevated temperature in the step (a) is in the range from 100° to 110° C.

In crude HFA hydrate subject to purification by a method according to the invention, every hydrate of HFA or FK is one formed by combination of at least 2.5 moles of water with 1 mole of HFA or FK. It is well known that alkali metal hydroxides readily react with HFA, and therefore it has been a common thought to avoid contacting HFA with any alkali metal hydroxide in preparing HFA from the viewpoint of preventing loss of HFA.

As the basis of the present invention we have discovered that, in the case of a mixture of HFA hydrate and FK's hydrates, every FK hydrate undergoes decomposition reaction with an alkali metal hydroxide while HFA hydrate hardly reacts with the same alkali metal hydroxide. That is, an alkali metal hydroxide added to such a mixture reacts preferentially with FK's hydrates.

The purifying method according to the invention is very suited to industrial practice and has many advantages such as simplicity of operations, shortness of time required for the decomposition of FK's hydrates and smallness of the loss of HFA hydrate.

DESCRIPTION OF THE PREFERRED EMBODIMENTS

The following is a detailed description of the purifying method according to the invention, wherein the decomposing agent is represented by sodium hydroxide which is preferred to other alkali metal hydroxides mainly for economical reasons.

In a crude HFA hydrate obtained by absorption of crude HFA gas industrially prepared by reaction between hexachloroacetone and hydrogen fluoride in water, usually the coexisting FK's hydrates amount to 0.1 to 10% of HFA hydrate depending on the reaction conditions employed in the preparation of HFA. Preparatory to the purifying operation according to the invention the hydrogen halides usually contained in the HFA gas and dissolved in the crude HFA hydrate solution are neutralized by the addition of a sufficient quantity of sodium hydroxide, for example, and the total content of FK's hydrates in the crude HFA hydrate is determined by sampling analysis.

For preferential and complete decomposition of FK's hydrates in the crude HFA hydrate, it is suitable to use such a quantity of NaOH that the mole ratio of NaOH to the total of FK's hydrates is in the range from 4:1 to 10:1, and preferably in the range from 6:1 to 8:1. When the mole ratio is between 4:1 to 10:1, NaOH amounts to about 30–70 mole% of the total organic matter (HFA and FK's) in the crude HFA hydrate. In the case of the hydrate of 5FK which is considered to undergo decomposition reaction with NaOH according to Equation (2), it suffices to use 4 moles of NaOH per 1 mole of the FK hydrate. However, it is usual that hydrates of 4FK and 3FK are contained together with 5FK hydrate and, therefore, it is preferable to increase the mole ratio of NaOH to the total of FK's hydrates to 6:1–8:1.

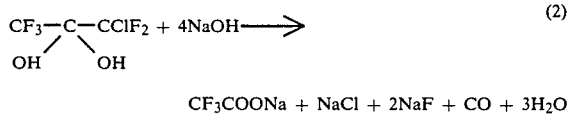

$$CF_3COONa + NaCl + 2NaF + CO + 3H_2O$$

It is unfavorable to use more than 10 moles of NaOH per 1 mole of FK's hydrates because of being uneconomical and possibly promoting a competitive decomposition reaction of HFA hydrate as represented by Equation (3). It is also unfavorable that NaOH amounts to more than 100 mole% of the total organic matter in the crude HFA hydrate because of promoting the decomposition of HFA hydrate.

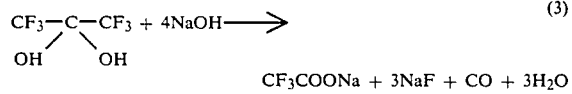

$$CF_3COONa + 3NaF + CO + 3H_2O$$

The manner of addition of NaOH to the crude HFA hydrate is not particularly specified, but it is convenient for practical operations to use an aqueous solution of NaOH, which can easily be introduced into the purifying apparatus by means of a pump. There is no specific limitation on the concentration of the NaOH solution. After the addition of a predetermined quantity of NaOH the decomposition reactions between FK's hydrates and NaOH take place spontaneously and proceed even at room temperature. However, at temperatures below about 70° C. the rates of the decomposition reactions are very low and hardly acceptable from a practical point of view. Therefore, it is preferred to carry out the decomposition of FK's hydrates with NaOH at a temperature in the range from 100° to 110° C., and more specifically at nearly the boiling point of HFA.3H$_2$O, 106° C. It is favorable that the mole ratio of water to HFA in the reaction system is between about 3 and about 10 also from the viewpoint of minimizing the loss of HFA hydrate. Stirring of the liquid under reaction is not a requisite, but it is desirable to perform stirring at least during the addition of NaOH to thereby ensure uniform dispersion of NaOH in the crude HFA hydrate liquid. The pressure at which the purifying operation is carried out is not a matter of importance. It is optional to employ a super-atmospheric pressure, but there is no advantage in doing so. Usually it is convenient to carry out the decomposition reactions of FK's hydrates by reflux of the HFA hydrate liquid at atmospheric pressure in a reactor provided with a simple reflux apparatus, and by this method the reaction temperature can easily be controlled. The addition of NaOH to the crude HFA hydrate may be completed before heating the HFA hydrate, or may alternatively be done while the crude HFA hydrate is under reflux and stirring.

By the above described simple procedure, the FK's hdrates coexisting the HFA hydrate are preferentially and completely decomposed. After completion of the decomposition of the FK's hydrates, the excess NaOH in the reaction liquid is neutralized by the addition of an adequate amount of a mineral acid such as sulfuric acid, phosphoric acid or hydrochloric acid to thereby prevent the decomposition of HFA hydrate. After that purified HFA hydrate is recovered by distillation of the treated liquid.

As can be seen in Equation (2), the solid residue recovered from the purifying process contains CF$_3$COONa together with NaCl and NaF. Accordingly trifluoroacetic acid CF$_3$COOH can be recovered from the solid residue by treatment with sulfuric acid.

The above described particulars of the purifying method using NaOH as the decomposing agent hold entirely similarly also when KOH or any other alkali metal hydroxide is employed as the decomposing agent. However, the use of KOH which is more costly than NaOH does not offer any appreciable advantage over NaOH in respect of the purification of HFA hydrate, and there is no reason for using a still more costly alkali metal hydroxide.

The invention will further be illustrated by the following nonlimitative examples.

EXAMPLE 1

The synthesis of HFA by reaction between hexachloroacetone and hydrogen fluoride gas was performed in the customary manner. Absorption of the crude product gas in water, followed by neutralization of hydrogen halides contained in the gas and dissolved by water using a sufficient quantity of sodium hydroxide, gave a crude HFA hydrate liquid of the following composition (by mole).

HFA hydrate: 91.0%
5FK hydrate: 6.3%
4FK hydrate: 2.1%
3FK hydrate: 0.6%

The ratio of water to the total organic matter was 4.2 by mole.

Then, 28.6 g of 19% aqueous solution of sodium hydroxide was added to 48.4 g of the crude HFA hydrate liquid. That is, the added NaOH was 5.44 g in absolute quantity and amounted to 750 mole% of the FK's hydrates and 67.5 mole% of the total organic matter in the crude HFA hydrate liquid. The resultant mixed solution was subjected to reflux for 2 hr at 105°–106° C. to cause NaOH to react with the FK's hydrates. After that 1.33 g of concentrated sulfuric acid (98%) was added to the reaction system to neutralize excess NaOH. By distillation of the liquid after the reaction, pure HFA hydrate was obtained at a recovery rate of 94.2% on the basis of the quantity of HFA hydrate contained in the crude HFA hydrate liquid.

EXAMPLE 2

The crude HFA hydrate liquid described in Example 1 was treated substantially in the same manner as in Example 1, except that the reflux operation was started before the addition of the NaOH solution and that the entire quantity (28.6 g) of the NaOH solution was added while the hydrate liquid was under reflux. In this case pure HFA hydrate was obtained at a recovery rate of 93.9%.

EXAMPLE 3

A crude HFA hydrate liquid of the following composition (by mole) was subjected to purification.
HFA hydrate: 91.3%
5FK hydrate: 7.0%
4FK hydrate: 1.5%
3FK hydrate: 0.2%
The ratio of water to the total organic matter was 4.1 by mole.

First, 68.2 g of 10% aqueous solution of potassium hydroxide was added to 48.3 g of the crude HFA hydrate liquid. That is, the added KOH was 6.82 g in absolute quantity and amounted to 700 mole% of the FK's hydrates and 61 mole% of the total organic matter in the crude HFA hydrate liquid. The resultant mixed solution was subjected to reflux for 2 hr at 105°–106° C. to cause KOH to react with the FK's hydrates. After that 1.0 g of concentrated sulfuric acid (98%) was added to the reaction system to neutralize excess KOH. By distillation of the liquid after the reaction, pure HFA hydrate was obtained at a recovery rate of 90.5%.

EXAMPLE 4

First, 22.1 g of 13% aqueous solution of NaOH was added to 48.3 g of crude HFA hydrate liquid described in Example 1. That is, the added NaOH was 2.90 g in absolute quantity and amounted to 400 mole% of the FK's hydrates and 36 mole% of the total organic matter in the crude HFA hydrate liquid. The resultant mixed solution was subjected to reflux for 2 hr at 105°–106° C. At the end of this operation, analysis of a sample revealed that the composition of the organic matter in the reaction liquid was as follows (by mole).
HFA hydrate: 92.9%
5FK hydrate: 2.1%
Trifluoroacetic acid: 5.0%

Since the decomposition of the FK's hydrates was incomplete, the reflux operation was continued for additional 8 hr at the same temperature. This operation resulted in complete decomposition of the FK's, so that the distillation of the treated liquid gave pure HFA hydrate.

COMPARATIVE EXPERIMENT

In this case, 6.4 g of $Na_2CO_3$ was added to 48.4 g of the crude HFA hydrate liquid described in Example 1 while the liquid was stirred. That is, the mole ratio of Na to FK's hydrates was 7. The resultant suspension was subjected to reflux for 2 hr at 105°–106° C. At the end of this operation, analysis of a sample revealed that the composition of the organic matter in the reaction system was as follows (by mole).
HFA hydrate: 94.9%
5FK hydrate: 4.7%
4FK hydrate: 0.3%
3FK: -

Since considerable amounts of FK's hydrates remained undecomposed, the reflux operation was continued further and analysis of the composition was made at suitable time intervals. The FK's hydrates gradually decreased, but even after the lapse of 10 hr from the recommencement of the operation the organic matter contained 0.2% of 5FK hydrate. The reaction mixture was in a state of slurry containing a relatively large amount of solid matter precipitated during the reaction and dispersed in HFA hydrate, so that filtration was needed precedent to distillation. Pure HFA hydrate was obtained by distillation of the filtrate, but the recovery was only 82%.

What is claimed is:

1. A method of purifying crude hexafluoroacetone hydrate which is practically free of hydrogen halides and contains at least one chlorofluoroacetone hydrate as impurity, the method comprising the steps of:
   (a) adding an alkali metal hydroxide to the crude hexafluoroacetone hydrate and maintaining the resultant mixed solution at an elevated temperature in the range of from about 100° C. to about 110° C. to thereby cause a preferential decomposition reaction of said at least one chlorofluoroacetone hydrate with said alkali metal hydroxide, wherein the mole ratio of said alkali metal hydroxide to the total of said at least one chlorofluoroacetone hydrate is in the range of from 4:1 to 10:1, and said alkali metal hydroxide amounts to 30–70 mole% of the total organic matter in the crude hexafluoroacetone hydrate;
   (b) neutralizing an excess portion of said alkali metal hydroxide by adding a mineral acid to the reaction liquid after step (a) to thereby prevent decomposition of the hexafluoroacetone hydrate; and
   (c) recovering purified hexafluoroacetone hydrate from the reaction liquid after step (b).

2. A method according to claim 1, wherein said mole ratio is in the range of from 6:1 to 8:1.

3. A method according to claim 1, wherein the crude hexafluoroacetone hydrate added with said alkali metal hydroxide is subjected to reflux until completion of said decomposition reaction.

4. A method according to claim 1, wherein said alkali metal hydroxide is sodium hydroxide in the form of an aqueous solution.

5. A method according to claim 1, wherein said mineral acid is selected from the group consisting of sulfuric acid and phosphoric acid.

* * * * *